United States Patent [19]
Carter

[11] Patent Number: 6,152,940
[45] Date of Patent: Nov. 28, 2000

[54] BALLOON MEMBER FOR CERUMEN REMOVAL

[76] Inventor: Stephen A. Carter, 10331 Cedar Bend Dr., San Antonio, Tex. 78245

[21] Appl. No.: 09/162,840

[22] Filed: Sep. 29, 1998

[51] Int. Cl.$^7$ ........................................................ A61F 9/00
[52] U.S. Cl. ............................................. 606/162; 604/96
[58] Field of Search ........................... 606/162, 94, 192; 623/1; 604/96, 175; 128/344, 325

[56] References Cited

U.S. PATENT DOCUMENTS

| | | | |
|---|---|---|---|
| 4,271,839 | 6/1981 | Fogarty et al. | 128/344 |
| 4,318,410 | 3/1982 | Chin | 128/325 |
| 5,112,310 | 5/1992 | Grobe | 604/175 |
| 5,662,607 | 9/1997 | Booth et al. | 604/96 |
| 5,669,936 | 9/1997 | Lazarus | 623/1 |
| 5,788,703 | 8/1998 | Mittelmeier | 606/94 |
| 5,871,467 | 2/1999 | Reuning et al. | 604/96 |

Primary Examiner—Michael Buiz
Assistant Examiner—Anthony S. King
Attorney, Agent, or Firm—Jackson Walker LLP

[57] ABSTRACT

A device for removing accumulated cerumen and a method for using the same, which device consists of a small balloon-tipped catheter inserted directly over the tip of a syringe or through the use of a plastic insert extended over the tip of a syringe, which balloon tip, when deflated, will fit easily into the auditory canal and, when inflated by depressing the plunger of the syringe, will provide a base for, when the syringe is removed from the ear canal, accumulating the blockage or excess cerumen thereon.

13 Claims, 3 Drawing Sheets

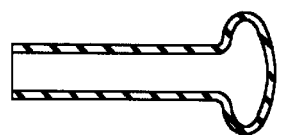
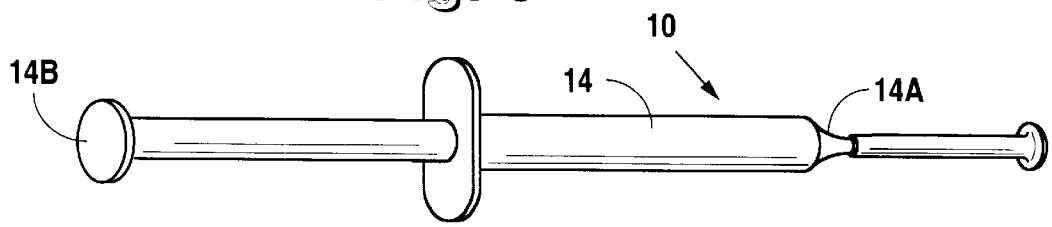
Fig. 6
Fig. 7
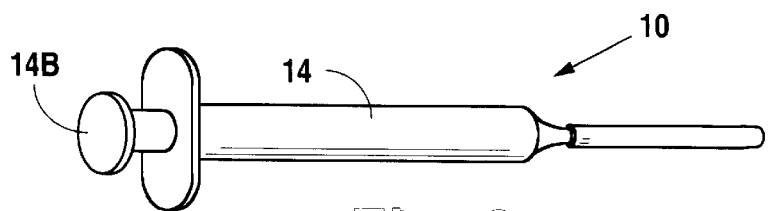
Fig. 8
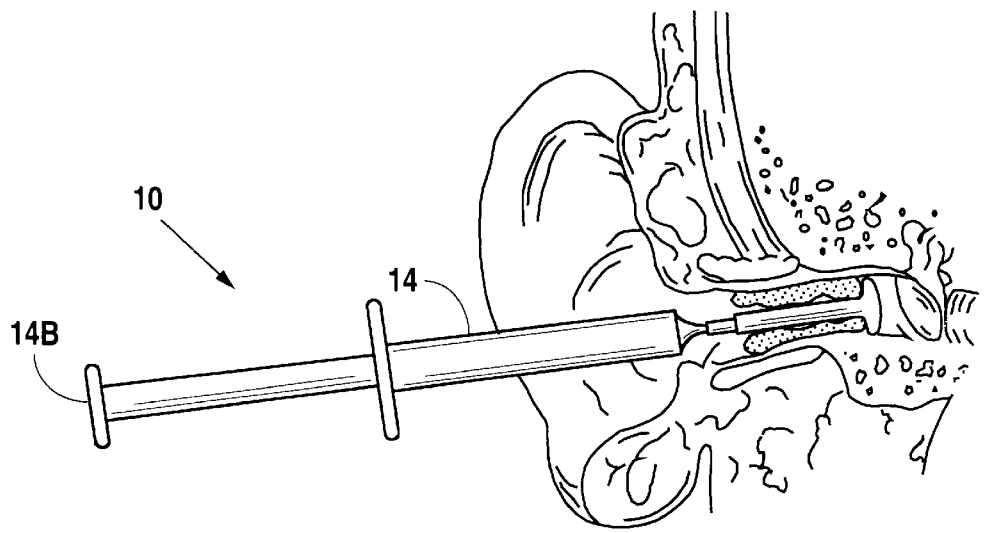
Fig. 9
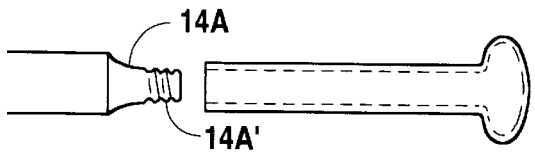
Fig. 10

6,152,940

BALLOON MEMBER FOR CERUMEN REMOVAL

FIELD OF THE INVENTION

This invention relates to a method and device for cerumen (wax) removal; more particularly, this invention is related to a device in the nature of a balloon-tipped catheter for insertion into the ear, inflation, and removal therefrom.

BACKGROUND OF THE INVENTION

Sebaceous glands secrete cerumen which contains lipids which collect in the ear canal. It is helpful that impactions or excess accumulations of cerumen be removed from the auditory canal prior to an ear examination. Such removal also facilitates a patient's hearing.

Presently, most physicians irrigate the auditory canal with a softening solution followed by the physical insertion of a small spatula or spoon-shaped device to scrape the excess cerumen from the walls of the auditory canal.

While this method of wax removal is usually satisfactory, it does run the risk of scraping or harming the tender lining of the auditory canal and does require some degree of physical dexterity and experience.

Because of such limitations, it will be seen to be helpful to healthcare personnel to have for their use a device which is simple to use, easy to construct, and effective to remove excess cerumen from the auditory canal of the patient.

Applicant provides herein for such a device and for a method for using the same, which device consists of a small balloon-tipped catheter placed directly over the tip of a syringe (or other source of air pressure), or through the use of a plastic insert extended over the tip of the syringe, which balloon tip, when deflated, will fit easily into the auditory canal and, when inflated (as by depressing the plunger of the syringe), will provide a base for accumulating excess cerumen when the syringe is removed from the auditory canal.

OBJECTS OF THE INVENTION

It is an object of the present invention to provide for a device for removing cerumen accumulations from the auditory canal of the ear and a method of using such device.

It is another object of the present invention to provide for an inflatable member which, deflated, fits into a cerumen-containing auditory canal and, when inflated and removed therefrom, will remove some of the cerumen.

It is yet another object of the present invention to provide a method for softening the cerumen in the auditory canal and, by inserting and inflating an elastic membrane, for removal of cerumen therefrom.

SUMMARY OF THE INVENTION

The objects of the present invention may be provided for in a device including a syringe (or other source of positive air pressure) having a plunger (or other pressurizing means), a tip, and an inflatable balloon member (or other elastic air pressure responsive member), which member, in a deflated condition, is insertable into the: auditory canal of the ear and, when in an inflated condition, is slightly larger than (or at least contacts) the cerumen accumulations in the auditory canal so that, when removed therefrom, accumulated cerumen is on the surface thereof.

To accomplish the objects of the present invention, there is also provided a method including the steps of providing the cerumen removal device as described in the preceding paragraph, inserting the inflatable balloon member into the auditory canal until it is past most of the cerumen accumulation, inflating typically to a diameter beyond the cerumen accumulation, and then removing the balloon member from the auditory canal while allowing the cerumen to accumulate on the surface thereof.

BRIEF DESCRIPTION OF THE DRAWINGS

FIG. 6 illustrates an inflatable member for positioning on the end of a syringe or other source of air pressure, which inflatable member has a head enlarged in external diameter in a pre-inflated condition which will form, when subject to air pressure, an elongated portion.

FIGS. 7 and 8 are side elevational views of the inflatable elastomeric member illustrated in FIG. 6 and in use position (FIG. 7) ready to be withdrawn from the ear canal and in a position for insertion into the ear canal (FIG. 8), where, under air pressure, the enlarged head of the inflatable member is reduced in diameter.

FIG. 9 is a side elevational view of the inflatable member set forth in FIG. 6 in a position where it has been inserted into a cerumen-clogged ear canal.

FIG. 10 is a side elevational view of a threaded luer lock tip on a syringe tip for receipt of any of the inflatable members of Applicant's present invention thereon.

DETAILED DESCRIPTION OF THE PREFERRED EMBODIMENT

Figure 1:
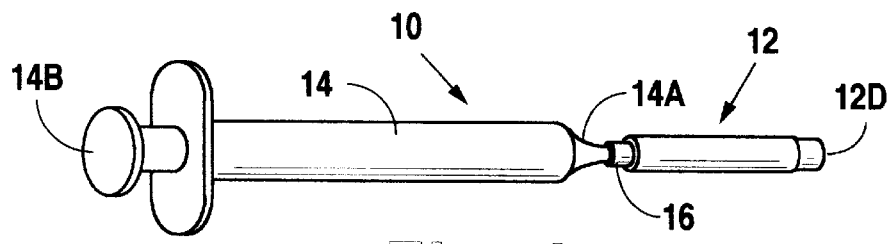
FIG. 1 is a perspective side view of the cerumen removal device of the present invention.

FIG. 1 illustrates a cerumen removal device 10 comprising an inflatable balloon member 12 fitted on a syringe 14 at a tip 14A thereof through, preferably but not necessarily, through the use of an open-ended sleeve 16 or other suitable adapter. Syringe 14 has a plunger 14B which, when depressed, will inflate closed end 12B of inflatable balloon member 12. The inflatable balloon member is typically made of rubber or other flexible, elastic, inflatable medium. That is, inflatable balloon member 12 has a deflated position and an inflated position which is achieved in response to air pressure provided by depressing plunger 14B.

Figure 2:
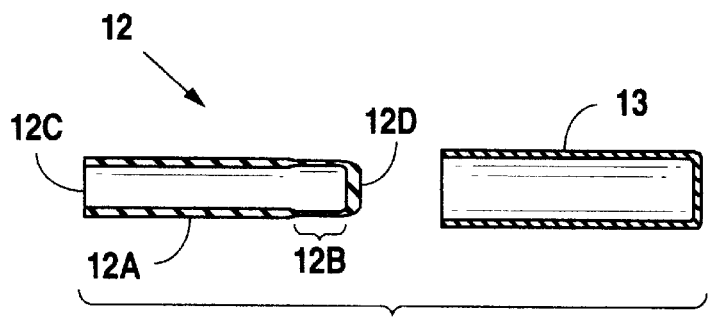
FIG. 2 is an exploded cross section, side elevational view of the inflatable balloon member of the present invention with a disposable cover shown dimensioned to be inserted thereover.

With reference to FIG. 2, it is seen that inflatable balloon member 12 is typically cylindrical and has walls defining a body portion 12A, a closed end 12B, an open end 12C, and a tip portion 12D. Further, it is seen that the closed end 12B may be comprised of walls defining a membrane, cylindrical in cross section, which membrane is typically thinner than the walls defining the remainder of the body portion 12A and also thinner than, typically, the tip portion 12D. The function of the thinner walls along the cylindrical portion of closed end 12B is to selectively allow inflation of that region when subject to air pressure through the syringe (see FIG. 3B).

Figure 3A:
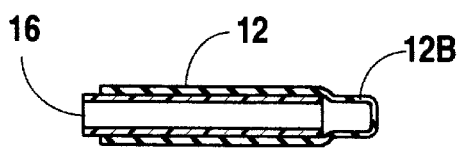
FIGS. 3A and 3B are cross section, side elevational views of inflatable the balloon member on a sleeve in a deflated (FIG. 3A) and an inflated (FIG. 3B) position.
Figure 3B:
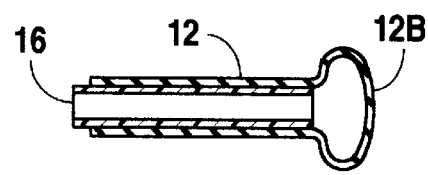

FIGS. 3A and 3B illustrate the deflated balloon member inserted onto sleeve 16 (FIG. 3A) and the inflated balloon member on sleeve 16 (FIG. 3B).

Figure 4:
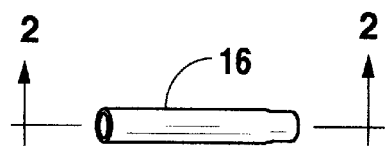
FIG. 4 is a perspective view of an open-ended sleeve for use with the syringe and inflatable balloon member of the present invention.

FIG. 4 illustrates details of open-ended sleeve 16, typically made of plastic and dimensioned for receipt therein, at one end thereof, of the tip 14A of syringe 14. The inflatable balloon member is dimensioned to slide snugly over the walls of either the sleeve, if one is used, or directly onto the walls of tip 14A of syringe 14. In the alternative, a luer lock connection system can be used to positively engage open end 12C of inflatable balloon member 12 to tip 14A of syringe 14.

The use of a luer lock connection is illustrated in FIG. 1 and is seen to comprise members engaging the walls of open end 12C and members engaging the walls of tip 14A of syringe 14, which members cooperatively engage with one another to positively lock either the inflatable balloon member or the sleeve to the tip of the syringe.

With the inflatable balloon member snugly on the sleeve and the sleeve affixed to the tip of the syringe in the manner set forth above, or with the inflatable balloon member directly attached to the tip of the syringe, either slideably (friction holding the two in place) or through the use of a luer lock connection or other suitable means, the depression of the plunger of the syringe will cause the tip of the inflatable balloon member to inflate to a diameter greater than body portion 12A of the inflatable balloon member.

Figure 5A:
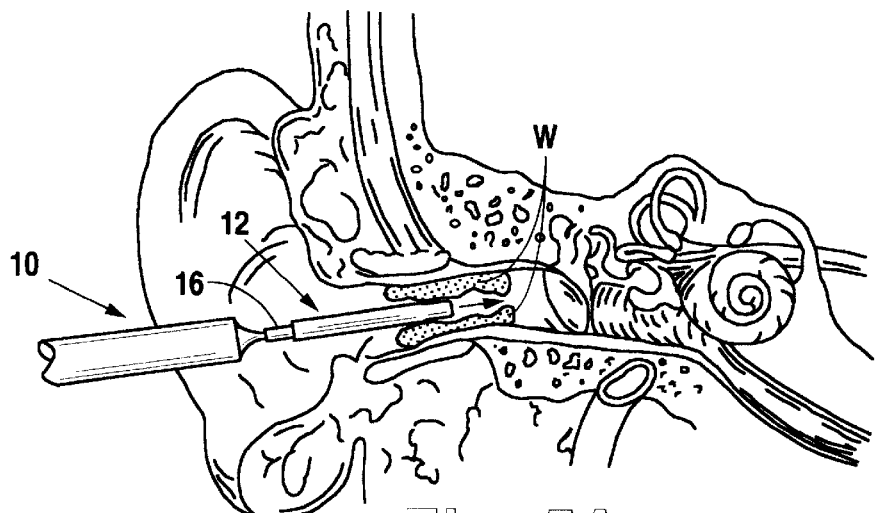
FIGS. 5A, 5B, and 5C are cross sectional, side elevational views of the method of using the unique device of the present invention to remove cerumen from the auditory canal of the ear, including inserting (FIG. 5A), inflating (FIG. 5B), and removing (FIG. 5C) the device from the ear of the patient.
Figure 5B:
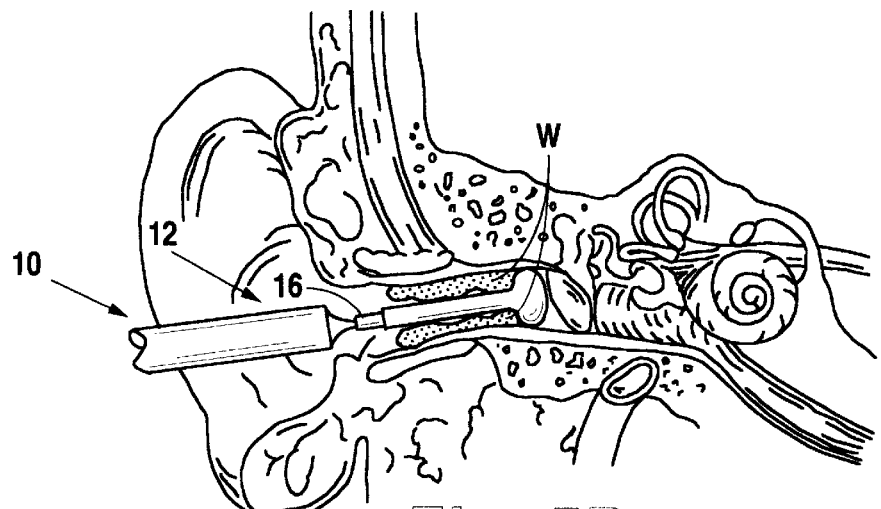
Figure 5C:
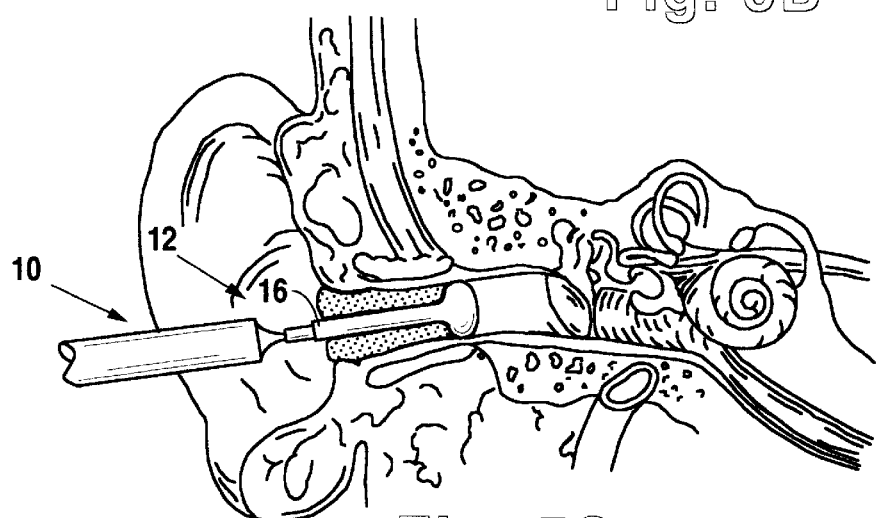

Given this structure of the cerumen removal device set forth above, FIGS. 5A, 5B, and 5C illustrate its usage. First, and typically, the ear may be irrigated with DEBROX® or other cerumen-softening solutions in ways known in the art. Second, with the inflatable balloon member in a deflated condition and affixed to tip 14A of syringe 14, either directly or through the use of luer lock connectors or other suitable positive engagement means, insertion of the inflatable balloon member is made into the ear.

Next, after the cerumen, obstruction, impaction, or accumulation has been cleared or, in any case, before the ear drum is reached, the physician will then gently depress plunger 14B until enclosed end 12C of the inflatable balloon member 12 is in the inflated position. At this point, the physician will slowly and carefully remove the inflatable balloon member from the auditory canal of the ear, where the tip of the inflatable balloon member, being inflated to a diameter greater than the impaction or cerumen accumulation area, or at least inflated until it snugly contacts the cerumen accumulation, will pick up the cerumen as illustrated in FIG. 5C.

The syringe used is typically a 5 cc syringe available, for example, from Beckton-Dickson or Tirumo Company. Beforehand, the healthcare professional can visually check the approximate size of the auditory canal and the obstructions therein to determine how much air should be injected in the inflation step of the cerumen removal.

Thus, the first step in using the novel device of the present invention for removing a cerumen accumulation is to provide a cerumen removal device comprising an inflatable balloon member engageable to the tip of a syringe, either directly or through the use of an open-ended sleeve or other adaptor. The cerumen is softened, typically by irrigating the ear with a cerumen softener. Following that, a visual inspection of the auditory canal is performed to determine the location and amount of cerumen accumulation and the approximate diameter of the auditory canal and the accumulation. The inflatable balloon member is then inserted into the auditory canal in a deflated condition, typically until it has passed the cerumen accumulation impaction area but is not inserted so far that it strikes or harms the tympanic membrane.

At this point, the physician depresses the plunger to insert an appropriate amount of air and inflate the tip of the inflatable balloon member. It is then removed slowly, allowing the excess cerumen to accumulate on the walls of the inflated tip.

The present invention also provides, as set forth in FIG. 2, a disposable cover 18 typically made of plastic or an elastomeric latex material which is shaped and dimensioned similar to that of the inflatable balloon member but with the diameter slightly larger. The disposable cover will slide over the inflatable balloon member when in use so that there is no contact between the inflatable balloon member and the patient, rather the disposable cover is what actually accumulates the cerumen thereon. In this way, the disposable cover may be thrown away and the inflatable balloon member may be used repeatedly.

An alternate preferred embodiment of Applicant's present invention, and its use, is illustrated in FIGS. 6 through 9. Applicant provides an inflatable member 12 which has a pre-inflated condition, including an enlarged head 13A. In this alternate preferred embodiment of inflatable balloon member 12, as illustrated in FIGS. 6 through 9, it is seen that when air pressure is applied to the inner walls of inflatable balloon member 12, enlarged head 13A is substantially eliminated, meaning its diameter is reduced so the entire member is generally straight, and may be inserted into the cerumen-clogged ear canal. In other words, air pressure is urged into the alternate preferred embodiment of inflatable balloon member 12 and it is essentially flattened out, in a condition capable of insertion into the ear canal. Subsequent removal of the air pressure from the interior of inflatable balloon member 12 will allow restoration of the original condition as set forth in FIG. 6. Removal then of the device from the ear canal will allow cerumen accumulation on the walls thereof.

FIG. 10 illustrates a luer lock mechanism on the tip of the syringe providing for self-threading of any inflatable balloon member on to the tip thereof.

Terms such as "left," "right," "up," "down," "bottom," "top," "front," "back," "in," "out," and like are applicable to the embodiments shown and described in conjunction with the drawings. These terms are merely for purposes of description and do not necessarily apply to the position or manner in which the invention may be constructed for use.

Although the invention has been described in connection with the preferred embodiment, it is not intended to limit the invention's particular form set forth, but on the contrary, it is intended to cover such alternatives, modifications, and equivalences that may be included in the spirit and scope of the invention as defined by the appended claims.

What is claimed is:

1. A device for cerumen removal, the device comprising:
   a syringe having a plunger and a tip; and
   an inflatable balloon member having a deflated position by an inflated position, and a remote end, wherein in the inflated position, the diameter of said remote end the balloon, as measured perpendicular to the axis of the syringe, is greater than the diameter of the inflated balloon as measured along the longitudinal axis of the syringe the inflatable balloon member capable of being engaged with the tip of the syringe and dimensioned for insertion into the auditory canal when in a deflated position;

wherein the inflatable balloon member is engaged with the tip of the syringe and inserted, deflated, into the auditory canal, and inflated and withdrawn to remove the cerumen accumulated in the auditory canal.

2. The device of claim 1 further including a disposable cover for placing over the inflatable balloon member and dimensioned to cover the inflatable balloon member when in the inflated position.

3. The device of claim 1 further including means for engaging the inflatable balloon member with the tip of the syringe.

4. The device of claim 3 further including a disposable cover for placing over the inflatable balloon member.

5. The device of claim 3 wherein the means for engaging includes a plastic sleeve dimensioned to snugly receive the inflatable balloon member over one end and on an outer surface thereof and for engagement with the tip of the syringe at another end thereof.

6. The device of claim 4 wherein the means for engaging includes a plastic sleeve dimensioned to snugly receive the inflatable balloon member over one end and on an outer surface thereof and for engagement with the tip of the syringe at another end thereof.

7. The device of claim 3 wherein the means for engaging the inflatable balloon member to the tip of the syringe includes a first luer lock means on the syringe and a second luer lock means on the inflatable balloon member, the two luer lock means for cooperatively and releasably engaging one another in a generally gas sealing manner.

8. The device of claim 7 further including a disposable cover for placing over the inflatable balloon member.

9. A method for removing cerumen accumulation from the auditory canal, the method including the steps of:

providing a syringe having a plunger and a tip, an inflatable balloon member having a deflated condition and an inflated condition, the inflatable balloon member and capable of being engaged with the tip of the syringe and dimensioned for insertion into the auditory canal when in the deflated condition;

inserting the inflatable balloon member in a deflated condition into the auditory canal;

inflating the inflatable balloon member to a position at least sufficient to contact the cerumen; and removing the inflatable balloon member from the auditory ear canal.

10. The method as set forth in claim 9 wherein the providing step also includes the step of providing a disposable cover to cover the inflatable balloon member and further includes the step of, following the engaging step and before the inserting step, covering the inflatable balloon member with the disposable cover.

11. The method as set forth in claim 9 further including, prior to the inserting step, the step of softening the cerumen of the ear.

12. The method as set forth in claim 9 wherein the providing step also includes the step of providing a disposable cover to cover the inflatable balloon member and further includes the step of, following the engaging step and before the inserting step, covering the inflatable balloon member with the disposable cover and further including the step of, prior to the inserting step, softening the cerumen of the ear.

13. A device for cerumen removal, the device comprising:

a syringe having a plunger and a tip; and an inflatable balloon member having a deflated position and an inflated position, the inflatable balloon member capable of being engaged with the tip of the syringe and dimensioned for insertion into the auditory canal when in a deflated position;

wherein the inflatable balloon member is engaged with the tip of the syringe and inserted, deflated, into the auditory canal, and inflated and withdrawn to remove the cerumen accumulated in the auditory canal and, further including a disposable cover for placing over the inflatable balloon member and dimensioned to cover the inflatable balloon member when in the inflated position.

* * * * *